United States Patent [19]

Moore et al.

[11] 4,169,123

[45] Sep. 25, 1979

[54] HYDROGEN PEROXIDE VAPOR STERILIZATION METHOD

[75] Inventors: Francis C. Moore; Leon R. Perkinson, both of Indianapolis, Ind.

[73] Assignee: Moore-Perk Corporation, Indianapolis, Ind.

[21] Appl. No.: 836,667

[22] Filed: Sep. 26, 1977

Related U.S. Application Data

[63] Continuation-in-part of Ser. No. 639,966, Dec. 11, 1975, abandoned.

[51] Int. Cl.$^2$ ............... A61L 13/00; A61K 33/40
[52] U.S. Cl. ................................ 422/29; 422/28; 422/32; 422/33; 424/130
[58] Field of Search .............. 21/57, 58; 424/130; 422/28, 32, 33, 29

[56] References Cited

U.S. PATENT DOCUMENTS

| | | | |
|---|---|---|---|
| 2,120,020 | 6/1938 | Coulter | 424/130 X |
| 2,193,622 | 3/1940 | Coulter | 424/130 |
| 2,368,806 | 2/1945 | Cook | 21/58 |
| 2,394,887 | 2/1946 | Berl | 21/58 UX |
| 3,328,312 | 6/1967 | Laycock et al. | 21/58 X |
| 3,854,874 | 12/1974 | Loliger et al. | 21/91 |
| 3,904,361 | 9/1975 | Egger | 21/57 |
| 3,912,451 | 10/1975 | Gaglea | 21/58 |
| 4,013,410 | 3/1977 | Thomas et al. | 21/58 |

*Primary Examiner*—Barry S. Richman
*Attorney, Agent, or Firm*—Tilton, Fallon, Lungmus & Chestnut

[57] ABSTRACT

A method of sterilizing the surfaces of articles such as medical intruments and other products by exposing such surfaces to hydrogen peroxide gas at temperatures below 80° C. in a temperature range that is generally considered nonsporicidal.

8 Claims, No Drawings

HYDROGEN PEROXIDE VAPOR STERILIZATION METHOD

This application is a continuation-in-part of Ser. No. 639,966, filed Dec. 11, 1975, now abandoned.

BACKGROUND OF THE INVENTION

Hydrogen peroxide in liquid form has long been regarded as a disinfectant or antiseptic which is generally unstable in vitro and transient in action in vivo. In general, efforts to increase its usefulness as an antiseptic have been directed towards increasing its stability in solution and controlling its rate of decomposition. E. A. Brown, Ohio State Med. J., 42:600 (1946). While pure hydrogen peroxide of any concentration, in the absence of contaminating catalysts and in a thoroughly clean container of non-catalytic material, is relatively stable, the use of such a liquid would normally eaxpose it to any of a variety of substances which trigger its decomposition. The addition of stabilizers such as sodium stannate or 8-hydroxyquinoline, each in the presence of a soluble pyrophosphate or a phosphate-pyrophosphate mixture, reduces catalytic decomposition but, even with such stabilizers, liquid hydrogen peroxide has received only limited attention in terms of its effectiveness in killing the more resistant organisms such as bacterial spores. Toledo et al., Applied Microbiology, 26:592-7 (1973); Swartling et al., J. of Dairy Research, 35:423-8 (1968); Wardle et al., Applied Microbiology, 30:710-11 (1975).

While the use of hydrogen peroxide aerosols has been reported (see Nasa Technical Translation TTF-15, 127, of Fedyayev et al., Virucidal Action of Hydrogen Peroxide Aerosols in Decontamination of Air in an Influenza Nidus, Zhurnal Mikrobiologii, Eipidemologii i Immunobiologii, 9:137-142 (1972)), such aerosols have been presented as simply a method of dispersing the liquid so that such liquid might then perform its disinfecting function. Where surfaces are to be disinfected, efforts have been made to be certain that they are wetted by the hydrogen peroxide mist; where air (as in a room) is to be disinfected, the duration of treatment has generally been measured by the sedimentation time for most of the aerosol from the air in the room (approximately 45 minutes). The emphasis in any event has been on treatment with liquid hydrogen peroxide solutions and their possible effects in achieving the desired results.

The low tissue toxicity of the decomposition products (water and oxygen) of hydrogen peroxide is a main reason why hydrogen peroxide has received attention in the past for use as a disinfectant or antiseptic, but the instability of previous hydrogen peroxide formulations appears to have caused a diminution interest as to their ability to act as sterilizing agents. See W. C. Schumb et al., Hydrogen Peroxide, 614 et. seq. (Reinhold, 1955). Instead, other techniques have been relied upon where sterilization has been required, for example, ethylene oxide treatment, radiation, and steam sterilization. Unfortunately, such techniques are unsuitable where the articles to be sterilized are themselves incapable of withstanding the sterilizing conditions or agents, or where no harmful residuals must be present following such treatment.

U.S. Pat. Nos. 3,854,874 and 3,904,361 describe processes for sterilizing a web of packaging material by dip coating the web in a concentrated solution (10% to 40%) of hydrogen peroxide and then quickly evaporating the liquid film within 20 seconds as it travels through a hot chamber at temperatures of 80° C. to 120° C. where some hydrogen peroxide gas is generated for contact with the web.

Submersion of the web in concentrated liquid hydrogen peroxide solution appears to cause a shock effect on microorganisms, making them easier to kill in the hot chamber. Also, at 80° C., heat alone starts to become sporicidal and its sporicidal activity increases with temperature. It is noted that steam sterilization is carried out at 120° C. to 125° C. Although hydrogen peroxide gas is generated for contact with the packaging web, it is believed that sterilization occurs because of the combined *liquid* and *heat* treatment.

Temperatures below 80° C. are generally considered nonsporicidal and a "cold" sterilizing process would operate in this range. The conventional ethylene oxide gas sterilization process is considered a cold process and typically operates at about 55° C.

The processes disclosed in the above two patents reduce the viable bacterial spore population by only 5 log orders. The Food and Drug Administration (FDA) is currently recommending that all medical and surgical products be sterilized to a probability of survival for spores, which are the most resistant of cells to kill, of $10^{-6}$ or better. This means that the sporicidal activity of a sterilizing process must be so reliable as to assure the probability of less than 1 organism out of 1,000,000 will survive a sterilization cycle.

SUMMARY OF THE INVENTION

The present invention deals with the discovery that hydrogen peroxide *gas* alone can be used to sterilize the medical instruments and other products at moderate temperatures that are generally considered nonsporicidal. This sterilization method does not require (1) liquid shock treatment through submersion in concentrated hydrogen peroxide solution, or (2) elevated temperatures of 80° C. and above. The "cold" *gas* sterilization prcess may be used with porous packages for medical instruments and other articles in which the gas is infused into the packages from an external source. The process may also include evaporating liquid hydrogen peroxide within the package or other container to generate the sterilizing gas. The invention includes the discovery that hydrogen peroxide as a vapor has substantial penetrating characteristics and that while decomposition may occur when such a vapor impinges on many surfaces, or contacts any of a wide variety of substances, enough hydrogen peroxide gas penetrates into the pores of the articles, and through their gas-permeable wrappers or containers, to kill even the most resistant known forms of microbial life.

DETAILED DESCRIPTION

It is generally agreed that spores are more resistant to lethal agents than are other microorganisms. The term "sterilization" as used herein means a method for treating microorganisms so that the probability of survival of spores can be less than $1 \times 10^{-6}$. The sporicidal tests recommended by the Association of Official Analytical Chemists and by other organizations suggest that *Bacillus subtilis* (*globigii*) or *Clostridium sporogenes* be used, and the tests carried out in determining the results of the present invention are in accordance with those recommendations.

The method of this invention is particularly useful in sterilizing articles which, by their nature, or because their packaging, cannot be easily sterilized by standard procedures. For example, a plastic foam medical swab, packaged in a flexible wrapper, may be unsuitable for sterilization by radiation (because of adverse affect on the plastic), or by ethylene oxide (because of the same reason and also because of powerful harmful residuals), or by steam sterilization (because of the inability of the wrapper or its contents to withstand autoclaving temperatures and the increased internal pressure). Similarly, a plastic optical contact lens may be adversely affected by autoclaving temperatures.

The "cold" gas sterilizing process of this invention operates very effectively at less than 80° C. A very effective temperature range is 63° C. to 68° C. (145° F. to 155° F.). For certain articles, a temperature of 71° C. (160° F.) might be used if the package and article were unaffected at such temperature.

The duration of holding the gas at such temperature may vary considerably although in general a period of less than 24 hours is sufficient. This depends somewhat on the article to be sterilized. For instance, a multiple layer gauze pad may require a somewhat longer period of treatment in order to achieve adequate penetration. The concentration of the hydrogen peroxide and type of equipment used to hold it at a particular temperature (i.e., circulating air oven, microwave oven, etc.), are also factors bearing on the duration of time needed for sterilization.

Unlike prior methods involving hydrogen peroxide, the present method preferably avoids any direct contact between the liquid peroxide and the primary article to be treated. Sterilization is achieved through vapor contact. The precise mechanism by which sterilization is achieved is not fully known although it has been theorized that the effectiveness may result from the formation of free radicals. In any event, it is believed that the destruction or inactivation of microorganisms is accompanied by decomposition of the gaseous hydrogen peroxide molecules. Water vapor is also present, either because decomposition of hydrogen peroxide leads to the formation of water and oxygen as the decomposition products, or because the water of the aqueous peroxide solution also vaporizes, or both. Since the decomposition products (water and oxygen) are not found harmful to human tissue, the sterilization process of this invention is especially useful where the avoidance of harmful residuals is an important consideration, or where direct contact of the articles with liquids might cause discoloration or other undesirable effects.

Since hydrogen peroxide gas may decompose upon contact with a variety of surfaces or substances, it is believed important that the vapor used in this method of treatment be freshly generated. That objective may be easily accomplished by enclosing a predetermined quantity of an aqueous hydrogen peroxide solution (prepared with deionized water, preferably reverse-osmosis deionized water) in the same container which encloses the article to be sterilized. Moderate heating of the container and its contents promotes vaporization of the liquid, and the freshly-generated hydrogen peroxide vapor is then free to contact interior surfaces of the container and the exposed surfaces of the articles therein to sterilize all of such surfaces.

The concentration of the aqueous hydrogen peroxide solution should be within the range of 0.0001 percent by weight to about 35 percent by weight, the preferred range being about 0.01 percent to 30 percent. Hydrogen peroxide (USP) is available at 27 percent concentration, and can be used directly or diluted as desired.

While the invention may be carried out most effectively by volitilizing a quantity of liquid hydrogen peroxide within the container in which sterilization is to occur, with the hydrogen peroxide thereby generating a vapor pressure within the container, sterilization might also be achieved by generating the active vapor externally of the container and then introducing it into the container for treatment of the articles which are within the container. Thus, the container may take the form of an oven having a chamber for treatment of batches of articles to be sterilized, the hydrogen peroxide vapor introduced into the chamber by air displacement, and being evacuated from the chamber at the end of the treatment operation. Since the hydrogen peroxide vapor is capable of penetrating many gas permeable plastic films, the article to be treated within the oven may even be prepackaged in gas permeable wrappers.

It is believed that heating of the container (to a temperature below 80° C.) and its contents may be achieved in any suitable manner. Radiant energy may be transmitted to the container and its contents in microwave form as well as any other known manner.

The method of this invention is further revealed by the following illustrative examples:

EXAMPLE 1

Vaginal swabs having plastic handles and plastic foam head portions were sealed in wrappers formed of a laminate of polyethylene and regenerated cellulose (Cellophane). Three such swabs were sealed in each wrapper along with six milliliters of an aqueous solution of 4.58 percent hydrogen peroxide. Before sealing each package, one of the foam swab heads were cut and a *Bacillus subtilis* (*globigii*) spore strip fully inserted therein. Also, in each package, a second swab head was cut and a *Bacillus stearothermophilus* spore strip was fully inserted. The handle of the third swab of each package was cut to reduce the length of that swab, but no spore strip was inserted into the head. A total of 14 of such test packages were prepared, two each day for a period of seven days. Thereafter, the pairs of packages formed on each of the days were sealed within seven outer wrappers formed of polyethylene-coated paper. No hydrogen peroxide was placed between the inner and outer wrapper; however, before sealing each outer wrapper, a *Bacillus subtilis* (*globigii*) spore strip and a *Bacillus stearothermophilus* spore strip were taped to the outer surface of the inner wrapper. All 14 doube-wrapped packages were placed into a heating chamber and heated at a temperature of 140° F. (60° to 66° C.) for 24 hours.

In addition to the above, a control package was prepared following precisely the same procedure as described except that no hydrogen peroxide was placed into the inner wrapper, and the package was not heated. Following the heat treatment, all of the packages, numbered in the sequence in which they were prepared, were analyzed by a testing laboratory with the following results:

| Sample | Results |
| --- | --- |
| Swabs - short samples #1–14 | All 14 samples Negative |
| *B. Stearothermophilus* spore strips inside foam swabs #1–14 | All 14 samples Negative |

| Sample | Results |
| --- | --- |
| -continued | |
| B. Stearothermophilus spore strips | Samples 1 through 3 Positive, |
| taped on wrappers #1–14 | Samples 4 through 14 Negative |
| B. Subtilis spore strips inside foam swabs #1–14 | All 14 samples Negative |
| B. Subtilis spore strips taped on wrappers #1–14 | All 14 samples Negative |
| Swab Positive Control Sample | Positive |
| B. Stearothermophilus Positive Control inside foam swab | Positive |
| B. Stearothermophilus Positive Control taped on wrapper | Positive |
| B. Subtilis Positive Control inside foam swab | Positive |
| B. Subtilis Positive Control taped on wrapper | Positive |

The chart reveals sterility was achieved within each of the inner packages and in the outer wrappers in which heat treatment was undertaken within six days following packaging. Hydrogen peroxide could pass from the inner packages into the spaces between the inner and outer packages only as a vapor through the gas permeable walls of the inner wrappers.

EXAMPLE 2

A total of six double-wrapped packages were prepared on the same day following the procedure described in Example 1, each package comprising an outer wrapper enclosing a pair of inner packages each containing three vaginal swabs. Unlike Example 1, however, the six packages were not only prepared at the same time, but the amounts of 4.58 percent hydrogen peroxide placed in the inner packages were varied. Specifically, packages 1 and 2 each received one milliliter; 3 and 4, two milliliters; 5 and 6, three milliliters; 7 and 8, four milliliters; 9 and 10, five milliliters; and 11 and 12, six milliliters. After all test packages were completed, they were placed in a heating chamber and heated at 140° to 150° F. (60° to 66° C.) for 24 hours, except for a control package which received no hydrogen peroxide and no heat.

| Sample | Results |
| --- | --- |
| Swabs - short samples 1–12 | All Negative |
| B. Stearothermophilus spore strips inside foam swab 1–12 | All Negative |
| B. Stearothermophilus spore strips taped on wrappers 1–12 | Samples 2 and 9 Positive All others Negative |
| B. Subtilis spore strips inside foam swabs 1–12 | All Negative |
| B. Subtilis spore strips taped on wrappers 1–12 | All Negative |
| All Controls | All Positive |

EXAMPLE 3

Two envelopes were prepared, each having one wall formed of a translucent polyester-polyethylene laminate and the other wall formed of a gas permeable paper. Within each envelope were placed two smaller glassine envelopes, one containing two spore strips of B. stearothermophilus and B. subtilis, and the other containing a spore strip of B. pumilus. The small glassine envelopes were sealed and similar spore strips, corresponding to their contents, were secured to the outside of such envelopes. Thereafter, three milliliters of an aqueous solution of 4.58 percent hydrogen peroxide were poured into each of the larger outer envelopes, care being taken not to allow the liquid to contact either the spore strips or the glassine envelopes. The two outer envelopes were then sealed and both packages were placed in a heating chamber where they were heated at 140° to 150° F. (60° to 66° C.) until no liquid could be seen in either envelope (15 hours). A laboratory sterility check on all of the spore strips yielded negative results for all such strips. A control package, prepared in the same manner as described but without the introduction of hydrogen peroxide solution and without heating, yielded positive results.

EXAMPLE 4

Polyether polyurethane foam sponges were individually packaged in envelopes formed of 30 weight bleached kraft paper coated with 0.5 mil polyethylene. The foam sponges were cut and B. stearothermophilus spore strips inserted and concealed therein. The envelopes were then heat sealed and 10 ml of an aqueous solution of 0.05 percent hydrogen peroxide was injected into the bottom of each envelope. The envelopes were placed into a circulating air oven and maintained for 24 hours at 140° to 150° F. (60° to 66° C.). At the end of that interval, no moisture appeared in any of the envelopes. The laboratory testing of all spore strips produced negative results, indicating that sterile conditions prevailed in each of the samples.

EXAMPLE 5

A B. stearothermophilus spore strip was placed in the center of a 12 inch square piece of barweeve needle punched two ounce rayon. The rayon was folded around the spore strip until the strip was covered on all sides by at least six layers of material. A rubber band was then fastened about the bundle.

Four such bundles were prepared. Each was placed in an eight inch square plastic bag. In the first bag, five milliliters of an aqueous solution of three percent hydrogen peroxide was added without directly moistening the rayon. Thereafter, the bag was heat sealed and placed in a Sears microwave oven using about 600 watts of power as described by the manufacturer. The oven was turned on for 15 seconds. It is unknown whether the temperature rose to 80° C. or above during this microwave heating step. If a microwave oven is used in production for the sterilizing method of this invention, it is important that temperature controls be installed to hold the temperature to below 80° C. so as to reliably operate in a "cold" range that will not damage the article or its package.

The second bag was treated identically to the first, except that eight milliliters of the hydrogen peroxide solution were added to the bag. The third received similar treatment, except that 10 milliliters of hydrogen peroxide were added and the oven was turned on for 20 seconds rather than 15 seconds.

The fourth bag was handled in a manner similar to the first and second, except that no hydrogen peroxide was added. This bag served as a control. It was placed in the microwave oven for 15 seconds.

Laboratory testing of the spore strips of all three test bags revealed negative results (no evidence of spore growth) for the first, second, and third packages. Spore growth (positive result) was clearly evident from the fourth package.

Other examples setting forth data which may be helpful in revealing the best mode presently known for practicing the invention are found in a co-pending co-owned application Ser. No. 836,665, filed Sept. 26, 1977 in the names of Richard J. Forstrom and Michael D. Wardle, for "Cold" Gas Sterilization Process and Apparatus Therefor, and are reproduced herein as follows:

EXAMPLE 6

Thirty silk sutures and 30 procelain penicylinder carriers each inoculated with approximately $10^5$ mature spores of *Bacillus subtilis* var. *niger* were placed in a vessel under 25 in Hg negative pressure and an atmosphere of 1.1 mg $H_2O_2$/L was generated. After a 4 hour exposure at 55° C., testing of the carriers indicated them to be sterile.

EXAMPLE 7

Ten silk sutures and 10 porcelain penicylinder carriers each inoculated with approximately $10^5$ mature spores of *Bacillus subtilis* var. *niger* were placed in a vessel under 25 in Hg negative pressure and an atmosphere of 0.6 mg $H_2O_2$/L was generated. After a 2 hour exposure at 60° C., testing of the carriers indicated them to be sterile.

EXAMPLE 8

Same procedure as in Example 7, except that 1.1 mg $H_2O_2$/L and 0.5 hours exposure at 55° were used. All carriers were rendered sterile.

EXAMPLE 9

Same procedure as in Example 1 with the substitution of approximately $10^2$ mature spores of *Clostridium sporogenes* per carrier. All carriers were rendered sterile.

EXAMPLE 10

Approximately $10^6$ mature spores of *Bacillus subtilis* var. *niger* on spore strips were placed in a vessel under 25 in Hg negative pressure and 1.4 mg $H_2O_2$/L was generated. After 1 hour exposure at 22° C., testing of the carriers indicated them to be sterile.

EXAMPLE 11

Same procedure as in Example 10 but without vacuum. After 24 hours exposure at 22° C., testing of the carriers indicated them to be sterile. Sterility was *not* achieved within 6 hours exposure.

While the variables of time, temperature, and $H_2O_2$ vapor concentration can be varied, the ranges of operation are 0.1 to 75 mg $H_2O_2$ vapor/L with a preferred range of 0.1 to 50 mg/L; 20°–80° C.; and 60 seconds to 24 hours time. In commercial use, the temperature might be in the range of 45°–65° C. and the time 10 minutes to 2 hours. The negative pressure applied is preferably greater than 15 inches of Hg. All other information and data as disclosed in the above-identified co-owned co-pending application may be considered in connection with the practice of the present invention and such disclosure is incorporated herein by reference.

While in the foregoing we have disclosed embodiments of the invention in considerable detail for purposes of illustration, it will be understood by those skilled in the art that many of these details may be varied without departing from the spirit and scope of the invention.

We claim:

1. A method of "cold" gas sterilization which comprises: surrounding an article to be sterilized with hydrogen peroxide gas; and maintaining said gas in contact with such article at temperatures below 80° C. until such article is sterile, whereupon sterility of said article is established, and including the step of maintaining said article in a sterile condition protected from recontamination until use.

2. A method as set forth in claim 1, wherein the gas is maintained at temperatures above approximately 20° C.

3. A method as set forth in claim 1, wherein the gas is maintained in contact with such article for a period greater than 60 seconds.

4. A method of "cold" sterilizing an article not suited for total liquid submersion, comprising the steps of: encasing said article in a chamber; surrounding the article in the chamber with hydrogen peroxide gas; and maintaining such gas in contact with the article at temperatures below 80° C. until such article is sterile, whereupon sterility of said article is established and including the step of maintaining said article in a sterile condition protected from recontamination until use.

5. A method as set forth in claim 4, wherein the article is encased in a sealed sterilizer tank.

6. A method as set forth in claim 4, wherein the article is encased in a package with at least one portion of the package being pervious to passage of hydrogen peroxide, but impervious to microbial passage.

7. A method as set forth in claim 4, wherein the gas surrounding the article is generated by placing liquid hydrogen peroxide of a concentration in the range of 0.0001% to 35% within the chamber in an amount substantially less than required for total liquid submersion of the article; and vaporizing the hydrogen peroxide liquid within the chamber for gaseous contact for all exposed areas of the article.

8. A method as set forth in claim 7, wherein the liquid placed within the chamber has a hydrogen peroxide concentration of 0.01% to 30%.

* * * * *